United States Patent [19]

Bardenstein

[11] Patent Number: 4,743,255

[45] Date of Patent: May 10, 1988

[54] RADIOPAQUE INTRA-OCULAR LENS IMPLANT

[76] Inventor: David S. Bardenstein, 13330 Sherwood Dr., Huntington Woods, Mich. 48235

[21] Appl. No.: 921,353

[22] Filed: Oct. 20, 1986

[51] Int. Cl.⁴ .............................................. A61F 2/16
[52] U.S. Cl. ...................................................... 623/6
[58] Field of Search ................................... 623/6, 1, 66

[56] References Cited

U.S. PATENT DOCUMENTS

| | | | |
|---|---|---|---|
| 4,254,180 | 3/1981 | Kline | 623/1 X |
| 4,349,498 | 9/1982 | Ellis et al. | 623/66 X |
| 4,573,998 | 3/1986 | Mazzocco | 623/6 |
| 4,615,702 | 10/1986 | Koziol et al. | 623/6 |

FOREIGN PATENT DOCUMENTS

| | | | |
|---|---|---|---|
| 0069089 | 1/1983 | European Pat. Off. | 623/6 |
| 2556665 | 6/1977 | Fed. Rep. of Germany | 623/6 |

*Primary Examiner*—Ronald L. Frinks
*Attorney, Agent, or Firm*—Darby & Darby

[57] ABSTRACT

An intra-ocular device for implantation in the eye has a lens and substantially radiopaque flexible loops each attached to the lens, the loops being adapted to secure the lens in a position within the eye. Each radiopaque loop comprises a strand of a synthetic polymer, such as polypropylene, into which is incorporated a substantially radiopaque contrast medium, such as iodide, bromide or barium salts.

7 Claims, 2 Drawing Sheets

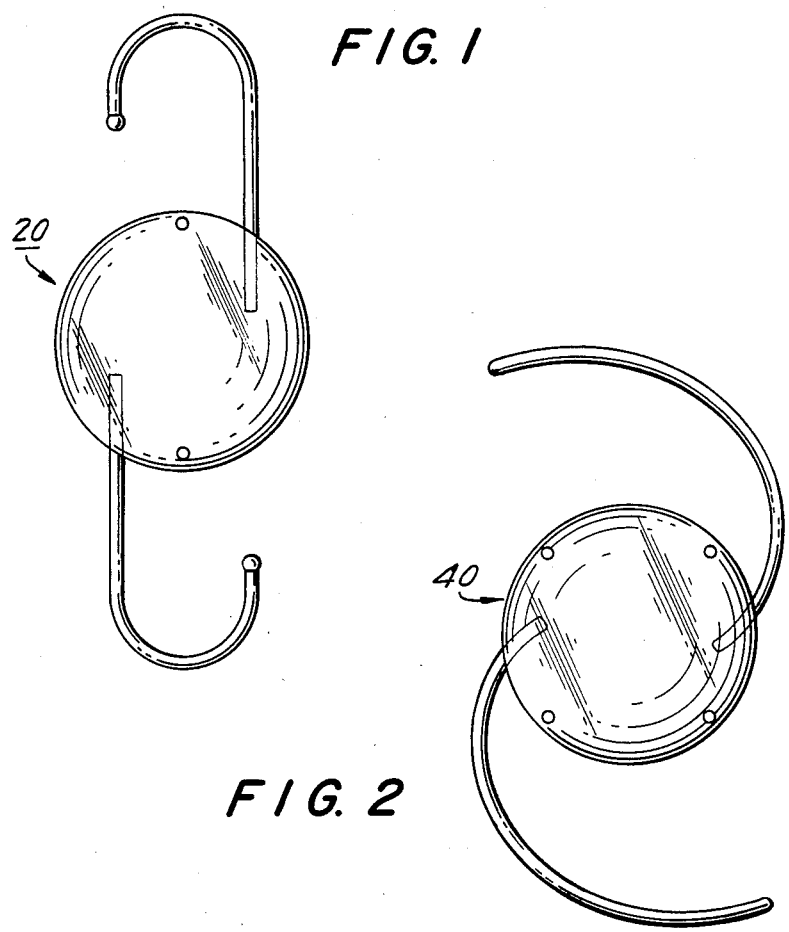
FIG. 1
FIG. 2
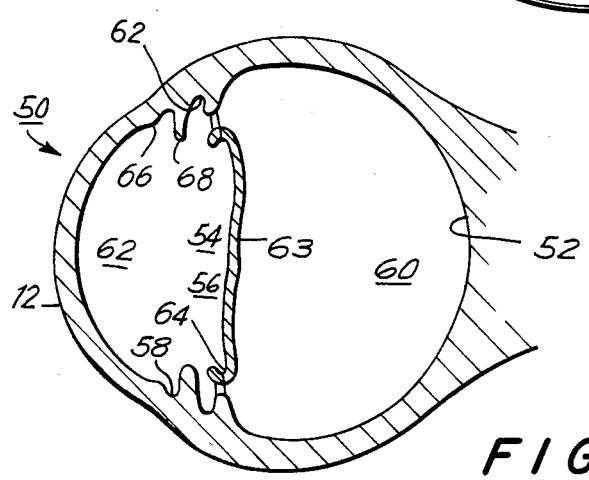
FIG. 3

RADIOPAQUE INTRA-OCULAR LENS IMPLANT

FIELD OF THE INVENTION

This invention relates generally to intra-ocular devices. In particular, the present invention is directed to an improved intra-ocular device which can be readily located in the eye even after a subsequent (post-operative) condition or injury to the eye which involves clouding or bleeding within the eye.

BACKGROUND OF THE INVENTION

In ophthalmic surgery, following removal of the lens of the eye, it is well known to implant an intra-ocular lens to take the place of the removed natural cataractous lens. Various types of lenses are in use, and several are described in Fechner and Alper, "Fechner's Intra-Ocular Lenses," published by Thieme, Inc., New York (1986), incorporated herein by reference in its entirety. Many lenses are also the subject of patents, including (as an illustrative sample only): Shearing, U.S. Pat. No. 4,159,546; Feaster, U.S. Pat. No. 4,418,431; Kelman, U.S. Pat. Nos. 4,174,543 and 4,370,760; Anis, U.S. Pat. No. 4,251,887; Ong, U.S. Pat. No. 4,365,360; and, Sheets, U.S. Pat. No. 4,328,595.

Intra-ocular lenses may be implanted at various locations within the eye, such as in the iris plane, or within the posterior chamber or within the anterior chamber. Lenses designed to be placed in the posterior chamber may be positioned in either the ciliary sulcus or the capsular bag of the eye. Many lenses, known as optics, are supported in the posterior chamber by two or more flexible filaments, known as haptics, which are secured to the optic, and which lodge against some adjacent portion of the eye. The haptics serve to position and retain the optic in its proper location. The haptics may also serve to position the lens implant in the anterior chamber by lodging in a groove formed by the scleral spur and the iris.

Unfortunately, subsequent post-implantation injuries or other conditions in which the implant is dislodged and the anterior, posterior or both chambers fill with blood or some other clouded medium, are known to occur. In these cases of traumatic dislocation, it becomes difficult for the surgeon to visually locate the intra-ocular lens implant. In many situations, location of the intra-ocular implant is impossible without the aid of time-consuming and highly sophisticated imaging techniques such as ultrasonic imaging or CT scanning. However, ultrasonic imaging is contraindicated in a ruptured globe, and CT scanning is expensive and delays surgery. Simple radiologic examination and diagnosis, such as by routine X-ray, is not helpful, as the materials used to fabricate presently known intra-ocular implants are substantially radiolucent.

An intra-ocular lens implant which could be accurately located by ordinary, quick and simple X-ray diagnostic techniques would be a major advance in the field of ophthalmic medicine, and would help solve a difficult and common problem faced by ophthalmic surgeons.

SUMMARY OF THE INVENTION

The present invention is an intra-ocular lens for surgical implantation into the human eye, which is marked with a radiopaque material in such a way that its position within the eye may be accurately determined by ordinary, preferably simple X-ray or other simple radiologic diagnosis, without resort to complex imaging techniques such as CT scanning or ultrasonic imaging.

The invention may be applied to any type of lens, preferably ciliary sulcus-fixated lenses and capsule-fixated lenses (two types of posterior chamber implants), but also lenses designed for placement in the anterior chamber. In particular, all or a part or parts of one or more of the lens haptics are impregnated with or contain a material which is detectable by simple X-ray examination. Each haptic may have a unique partially or substantially radiopaque pattern formed therein, thus allowing highly accurate position determination by the surgeon even when the eye is filled with an opaque fluid, such as blood.

BRIEF DESCRIPTION OF THE DRAWINGS

Other objects and advantages will be made clearer from the following detailed description of the preferred embodiments, taken in conjunction with the drawings, in which:

FIG. 1 is a front plan view of an intra-ocular lens implant in accordance with the present invention;

FIG. 2 is a front plan view of another intra-ocular lens implant according to the invention;

FIG. 3 is a simplified cross-sectional view of a human eye for facilitating understanding of the present invention;

DESCRIPTION OF THE PREFERRED EMBODIMENTS

Figure 4:
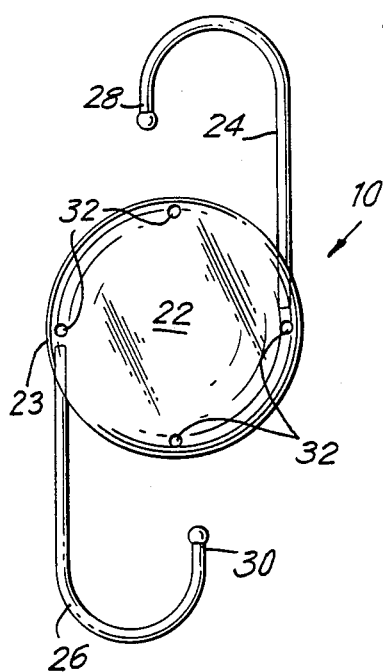
FIG. 4 is a more detailed front plan view of the device of FIG. 1.

Referring first to FIG. 3, reference 50 generally designates an eyeball shown in simplified cross-section, for ready understanding of the invention. It will be understood that structures of the eyeball not relevant to the invention has been omitted from FIG. 3.

The eyeball 50 includes a cornea 12, an iris 68 having a central opening or pupil 54, a lens capsular remnant or capsular bag 63, vitreous humor 60 and a retina 52. The natural lens, which normally lies behind the iris and is contained within the capsule forwardly of the capsular bag 63 has been omitted. An aqueous zone, between the cornea 12 and the capsular bag 63, is subdivided by the iris 68 into an anterior chamber 62 and a posterior chamber 56. A scleral spur 66 in the anterior chamber 62 is spaced from the iris 68 thereby defining a groove 58.

FIGS. 1, 2 and 4 show generally several different intraocular lens implants (20, 40, 10, respectively) having known shapes for the positioning and retaining of the central optic portion within the eye, as will be more clearly explained below. Referring to FIG. 4, the device 10 includes a lens 22 which is circular and has a peripheral rim 23. The front face of the lens 22 is convex. The rear face of the lens 22 may have a planar rim portion with the major surface thereof being convex. In many cases, one or more holes 32 are preferably spaced around the outer portion of the lens 22.

The lens 22 is preferably made from a transparent polymeric plastic material, preferably polymethylmethacrylate (PMMA)(e.g., PERSPEX CQ, a PMMA of the highest grade and purity for the implanted lens, specifically produced for medical use by the Imperial Chemical International Company), which is compatible, light, crystalline, transparent and resistant to aging or climatic change, liquid acids, bases, salt solutions, as well as to organic solvents.

The lens 22 is provided with an inferior haptic loop 24 and a superior haptic loop 26, the loops 24 and 26 being resiliently deformable in a direction radially of the lens 22. Each of the loops 24 and 26 has one end fixedly attached to the lens 22, preferably at the rim 23 in any conventional manner. Loop 24 has a free end 28 and loop 26 has a free end 30. In a customary implantation technique, the intra-ocular lens device 10 is implanted in the capsular bag 63 of the human eye 50, with the inferior and superior haptics 24 and 26 extending resiliently outwardly so as to engage the capsular bag 63.

As is seen in FIGS. 1 and 2, a principal difference between various intra-ocular implants is the size and shape of the haptic loops or support members. Other devices may include more than two haptic loops, or loops which are affixed at both ends to the optic. Additional distinctions may include the arcuate spacing of attachment points of the haptics to the optic, which in each of FIGS. 1, 2 and 4 is about 180°. Still other devices use vastly different support members such as fenestrated feet, frame assemblies, combinations of bent feet with closed loops, and sinuous filaments, for example.

According to the invention, the support members or haptic loops 24 and 26 are specially made so as to be radiopaque or substantially radiopaque, i.e., visible upon routine X-ray examination. Known materials for the fabrication of haptics, of suitable purity and quality for medical use, include various wire materials which are compatible, i.e., inert with respect to the eye fluid and tissue, such as nylon 6 (e.g., SUPRAMID, available from VIS-Kunststoffwerke Alfred Huber; PERLON, available from Perlon Leverkusen-Bayerwork); polypropylene (e.g., PROLENE, available from Carisbrook Industries, Inc.), polyethyleneglycol terephthalate (PETP)(e.g., MERSILENE, available from Johnson & Johnson), polyimides, and drawn monofilament polymethylmethacrylate. Other materials under investigation for use in constructing support members or haptics include silicone and polysulfone.

Whatever material is chosen for the haptic, the material is altered in a novel manner by the incorporation of a radiopaque substance so as to be partially or substantially radiopaque so that the haptics may be detected by simple X-ray. The use of radiopaque materials is well-known in other fields of medicine including joint arthrography and cardiac angiography, but until this invention, such materials have not been used in ophthalmic medicine applications such as are presently described.

While a light dense material, such as a thin metal wire, may be placed in the haptic, a preferred construction employs common contrast media such as iodide, bromide or barium salts impregnated into or formed as a central core within the haptic. Thus, a traumatically dislodged intra-ocular implant can be easily and rapidly located anywhere in the eye, through the use of routine X-ray diagnosis. An otherwise difficult and time-consuming task is therefore eliminated and the surgeon may almost immediately proceed to repair any damage caused before or by the traumatic dislocation of the device. This is most significant in situations where the passage of time adversely affects the outcome of the surgical procedures required.

In each of FIGS. 1, 2 and 4, the haptic loops (24 and 26 in FIG. 4) are specially radiopaque in non-specified patterns. FIGS. 5-8 illustrate different radiopaque patterns which may be used, it being understood that these patterns are illustrative samples only, and do not limit the scope of the invention in any way. Any pattern which is uniquely recognizable may be used. It is further understood that a great many different intra-ocular devices may enjoy the advantages and benefits of radiopaque marking, and that the invention is not limited to merely the illustrative preferred embodiments described herein.

Figure 5:
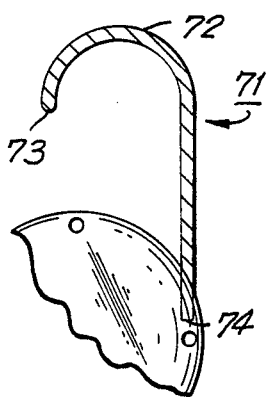
FIGS. 5-8 are various patterns of radiopaque marking of lens haptics according to the invention.
Figure 6:
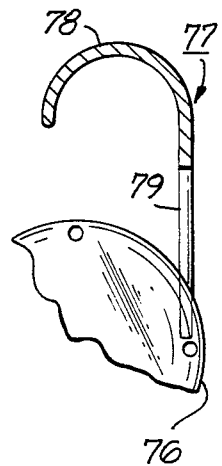
Figure 7:
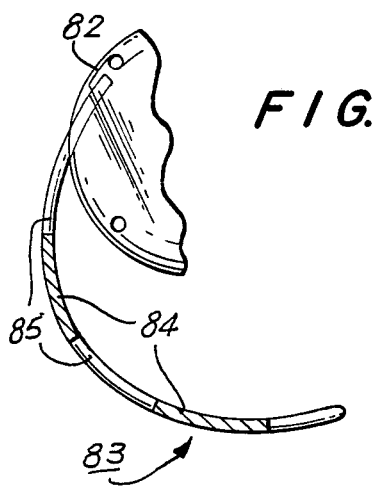
Figure 8:
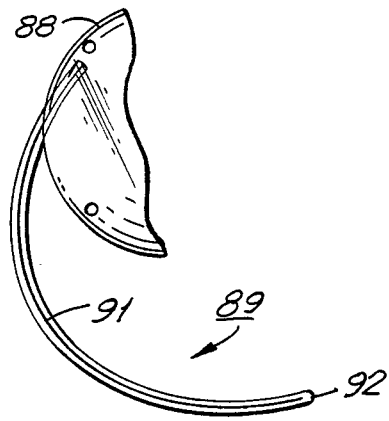

FIG. 5 shows a portion of an optic 70 to which a special haptic loop 71 is attached in a customary manner. The entire haptic 71 is radiopaque, from its free end 73 along its curved length 72 to the end 74 embedded in the optic 70. Such a structure may result from addition of the radiopaque substance to the material from which the haptic is formed, e.g., melted PMMA pellets before a monofilament is drawn. In FIG. 6, only the end portion 78 of the haptic loop 77 is radiopaque. The haptic end 79 attached to the optic is not specially radiopaque. Such a construction is useful where the radiopaque material is not compatible with the optic material. FIG. 7 shows a repetitive radiopaque pattern formed in the haptic loop 83 connected to the illustrated optic portion 82. In this case, radiopaque segments 84 alternate with radiolucent segments 85. FIG. 8 shows a central wire core 91 positioned within the haptic 89 attached to the optic portion 88. The extreme free tip 92 of the haptic 89 is preferably sealed so as to completely encapsulate the thin wire core. Many other patterns are possible. Also, each of the generally two or more haptics may be marked differently, so that in the case of special optics having asymmetrical features, the orientation of the device may be determined as well as its position within the eye.

The present invention may be embodied in other specific forms without departing from the essential attributes described above. For example, the radiopaque contrast medium may be incorporated directly into the optic, in the case of a contrast medium which is not light dense (in which case the optic would no longer be transparent). The invention is limited only by the appended claims.

I claim:

1. A device for implantation in the eye comprising: an intra-ocular lens; and
at least one support member attached to the lens, the support member comprising a filament of a synthetic polymer and containing an X-ray detectable substantially radiopaque material selected from the group consisting of iodide, bromide and barium salts, the support member being adapted to secure the lens in a position within the eye.

2. The device of claim 1, wherein the synthetic polymer is selected from the group consisting of nylon 6, polypropylene, polyethyleneglycol terephthalate, polyimide, and polymethylmethacrylate.

3. The device of claim 1, wherein the device is adapted to be implanted in the posterior chamber of the eye.

4. The device of claim 1, wherein the device is adapted to be implanted in the anterior chamber of the eye.

5. The device of claim 1, wherein the device is adapted to be implanted in the iris plane of the eye.

6. The device of claim 1, wherein the device has two radiopaque support members.

7. The device of claim 1, wherein the device has three radiopaque support members.

* * * * *